US012694984B2

(12) United States Patent
Birur et al.

(10) Patent No.: US 12,694,984 B2
(45) Date of Patent: Jul. 28, 2026

(54) SYSTEMS AND METHODS FOR END OF LIFE ANALYSIS

(71) Applicant: DIVERSIFIED HEALTH TECHNOLOGIES, LLC, Collierville, TN (US)

(72) Inventors: Theja Birur, San Ramon, CA (US); Terry Swatley, Collierville, TN (US); William Wilemon, Laguna Niguel, CA (US); Wayne Addison, Eads, TN (US); Michael Wills, Memphis, TN (US); David Boal, Canton, GA (US)

(73) Assignee: DIVERSIFIED HEALTH TECHNOLOGIES, LLC, Collierville, TN (US)

( * ) Notice: Subject to any disclaimer, the term of this patent is extended or adjusted under 35 U.S.C. 154(b) by 286 days.

(21) Appl. No.: 18/346,682

(22) Filed: Jul. 3, 2023

(65) Prior Publication Data

US 2024/0013917 A1     Jan. 11, 2024

Related U.S. Application Data

(60) Provisional application No. 63/486,606, filed on Feb. 23, 2023, provisional application No. 63/358,725, filed on Jul. 6, 2022.

(51) Int. Cl.
*G16H 50/20* (2018.01)
*G06F 40/40* (2020.01)
(Continued)

(52) U.S. Cl.
CPC ............. *G16H 50/20* (2018.01); *G06F 40/40* (2020.01); *G06N 20/00* (2019.01); *G16H 10/60* (2018.01)

(58) Field of Classification Search
CPC ........ G16H 50/20; G16H 10/60; G06F 40/40; G06N 20/00; G06N 3/09; G06N 5/01; A61B 5/7275
See application file for complete search history.

(56) References Cited

U.S. PATENT DOCUMENTS 8,244,654 B1 * 8/2012 Hobgood ............... G06Q 40/08
                                                            706/62
2018/0301221 A1 * 10/2018 Rothman ............... A61B 5/681

OTHER PUBLICATIONS

Beeksma et al., Predicting life expectancy with a long short-term memory recurrent neural network using electronic medical records, Feb. 28, 2019, BMC Medical Informatics and Decision Making, (2019) 19:36 (Year: 2019).*

(Continued)

*Primary Examiner* — Marc Q Jimenez
*Assistant Examiner* — Alexis K. Van Duzer
(74) *Attorney, Agent, or Firm* — NORTON ROSE FULBRIGHT US LLP

(57) ABSTRACT

Certain aspects of the present inventive concept are directed towards a data analysis system. The data analysis system includes a memory and one or more processors coupled to the memory, the one or more processors being configured to: obtain health information associated with at least one patient of a health facility; analyze the health information to determine a rate of health decline associated with one or more health parameters of the patient; generate at least one interface indicating whether the rate of health decline meets a threshold for each of the one or more health parameters, and output the at least one interface for display on a display device.

23 Claims, 15 Drawing Sheets

(51) Int. Cl.
    G06N 20/00          (2019.01)
    G16H 10/60          (2018.01)

(56)                References Cited

OTHER PUBLICATIONS

Shi et al., Assessing Palliative Care Needs Using Machine Learning
Approaches, 2021, IEEE (Year: 2021).*
"Hospice—Determining Terminal Status," Nov. 14, 2019, https://
www.cms.gov/medicare-coverage-database/view/lcd.aspx?LCDId=
33393&ContrId=272, accessed Sep. 26, 2024.

\* cited by examiner

502 — Obtain A First Plurality Of Input Features Indicating First Characteristics Associated With A Patient 504 — Analyze, Via A Machine Learning Component, The First Characteristics Based On The First Plurality Of Input Features 506 — Estimate An End Of Life Associated With The Patient Based On The Analyzing Patient Decline by Team

602

700

Patient: Wayne, Bruce

| Benchmark | Date 1 | Date 2 | Date 3 | Date 4 | Date 5 | Date 6 |
|---|---|---|---|---|---|---|
| Vital Signs | XX | XX | XX | XX | XX | XX |
| I's and O's | XX | XX | XX | XX | XX | XX |
| Fatigue | XX | XX | XX | XX | XX | XX |
| Weight/Measurers | XX | XX | XX | XX | XX | XX |
| Agitation | XX | XX | XX | XX | XX | XX |

800

Quality Reporting

| Clinical Team | Copy & Paste | Visit Standard | Note Discrepancy |
|---|---|---|---|
| Red | | | |
| Blue | ● | | ● |
| Gold | | ● | |
| Orange | ● | | ● |

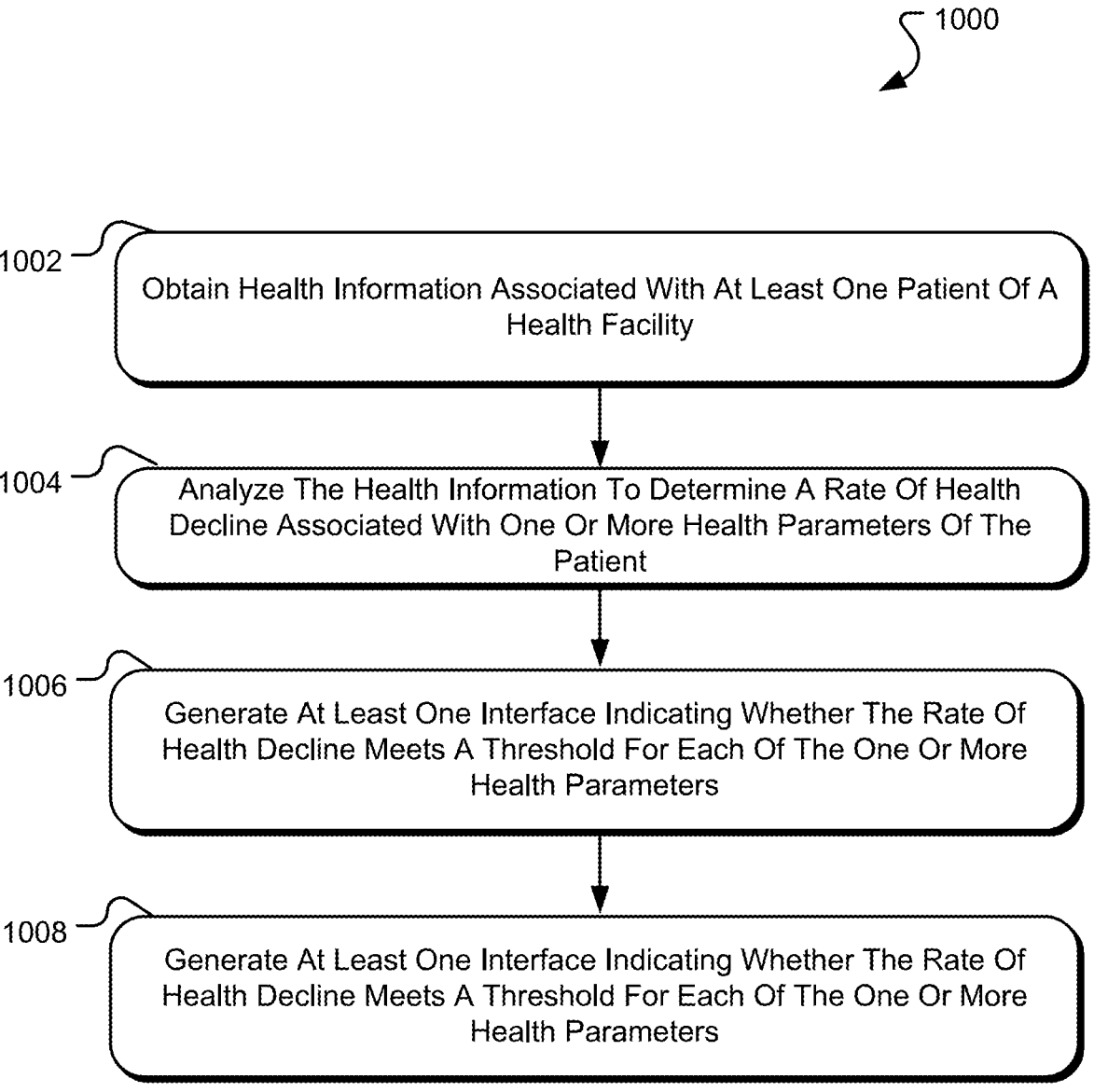

1000

1002 — Obtain Health Information Associated With At Least One Patient Of A Health Facility 1004 — Analyze The Health Information To Determine A Rate Of Health Decline Associated With One Or More Health Parameters Of The Patient 1006 — Generate At Least One Interface Indicating Whether The Rate Of Health Decline Meets A Threshold For Each Of The One Or More Health Parameters 1008 — Generate At Least One Interface Indicating Whether The Rate Of Health Decline Meets A Threshold For Each Of The One Or More Health Parameters

FIG. 10

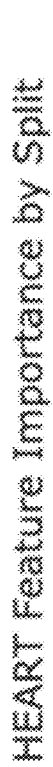
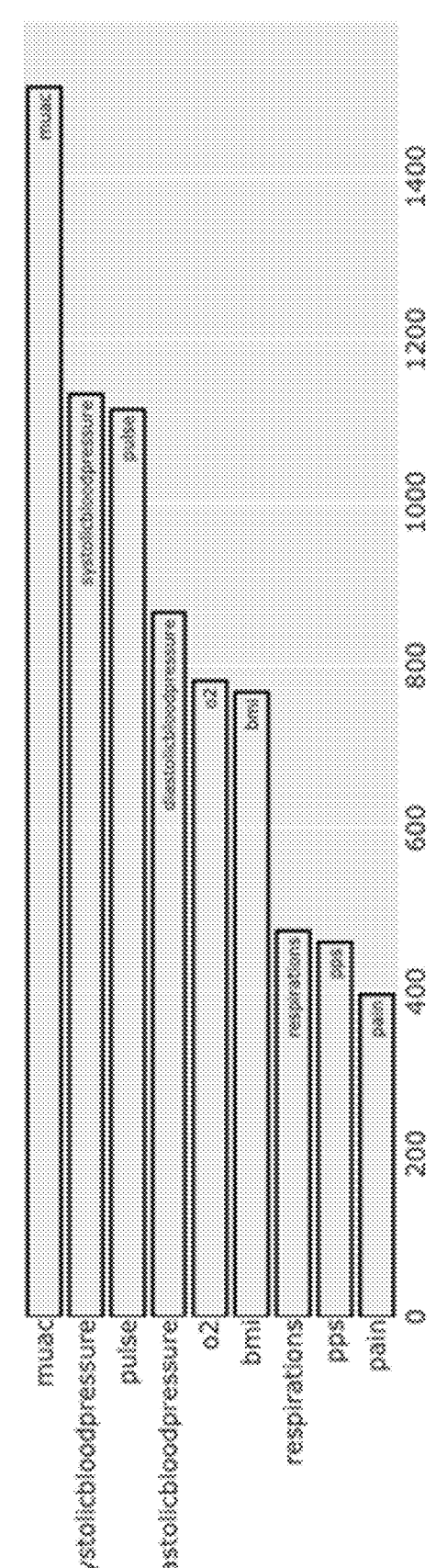
FIG. 12C

SYSTEMS AND METHODS FOR END OF LIFE ANALYSIS

CROSS REFERENCE TO RELATED APPLICATIONS

This application claims the benefit of U.S. Provisional Patent Application Ser. No. 63/358,725 filed Jul. 6, 2022, and U.S. Provisional Patent Application Ser. No. 63/486,606 filed Feb. 23, 2023, the disclosure of each are hereby incorporated by reference in their entireties.

BACKGROUND

1. Field

The present inventive concept relate to systems and methods for end of life analysis, and more particularly, to systems and techniques for analyzing data associated with end of life of patients.

2. Discussion of Related Art

Many terminally ill patients undergo end of life monitoring and treatment in a variety of settings. Hospice care is one form of medical care for patients who have been diagnosed with a life-limiting illness. The patient's comfort and symptom management become the primary focus, rather than finding a cure. Currently, most hospice patients are covered through the Medicare hospice benefit. Other terminally ill patients may receive treatment at a hospital or at home with a care taker.

Every year, the federal government announces the budget for that year for hospice coverage and other types of medical treatment for terminally ill patients. Federal Government has strict guidelines on who will qualify for hospice care and other types of medical treatment. For example, hospice coverage is for patients who the referring physician has deemed to live for a limited period of time. The budget allocation is a significant financial risk that cannot be effectively managed with current tools. Any Medicare payments that were received more than the aggregate cap are considered overpayments and must be repaid to Medicare by the hospice.

SUMMARY

Certain aspects of the present inventive concept are directed to a method for end of life prediction. The method generally includes obtaining a first plurality of input features indicating first characteristics associated with a patient, analyzing, via a machine learning component, the first characteristics based on the first plurality of input features, estimating an end of life associated with the patient based on the analyzing via the machine learning component to generate an estimate, and displaying the estimate via a display.

Certain aspects of the present inventive concept are directed to an apparatus for end of life prediction. The apparatus generally includes a memory and one or more processors coupled to the memory. The one or more processors being configured to obtain a first plurality of input features indicating first characteristics associated with a patient, analyze, via a machine learning component, the first characteristics based on the first plurality of input features, and estimate an end of life associated with the patient based on the analyzing.

Certain aspects of the present inventive concept are directed to a non-transitory computer-readable medium having instructions stored thereon that, when executed by one or more processors, cause the one or more processors to: obtain a first plurality of input features indicating first characteristics associated with a patient; analyze, via a machine learning component, the first characteristics based on the first plurality of input features; and estimate an end of life associated with the patient based on the analyzing. The first plurality of input features can include baseline input features and additional input features used for continuous monitoring Certain aspects of the present inventive concept are directed towards a data analysis system. The data analysis system includes a memory and one or more processors coupled to the memory, the one or more processors being configured to: obtain health information associated with at least one patient of a health facility; analyze the health information to determine a rate of health decline associated with one or more health parameters of the patient; generate at least one interface indicating whether the rate of health decline meets a threshold for each of the one or more health parameters, and output the at least one interface for display on a display device.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 10 is a flow diagram illustrating example operations for data analysis, in accordance with certain aspects of the present inventive concept.

FIGS. 12A-12C illustrate example key feature graphs corresponding to patient types, in accordance with certain aspects of the present inventive concept.

It will be apparent to one skilled in the art after review of the entirety disclosed that the steps illustrated in the figures listed above may be performed in other than the recited order, and that one or more steps illustrated in these figures may be optional.

DETAILED DESCRIPTION

Certain aspects of the present inventive concept are directed towards systems and techniques for predicting end of life of a patient. Prediction of end of life may be valuable in various suitable applications. For example, the ability to predict end of life allows hospice management to efficiently and more effectively make census and financial decisions. The present inventive concept describes a system that allows a provider to evaluate current and future operating status in real-time so they can make informed decisions to mitigate risk. A data analysis system described herein allows a provider to predict the future of patient-length-of-stay.

Conventional techniques for estimating end of life involve manual processes which may use spreadsheets and selecting a fixed number of days remaining for patients. The conventional techniques may lead to higher financial risk since it does not account for patients living longer than their estimated days. The data analysis system described herein provides, on-demand and in real-time, the ability to estimate each patient end of life. The estimate may be continuously updated by reviewing medical conditions as the medical professionals document their findings on each visit.

Figure 1:
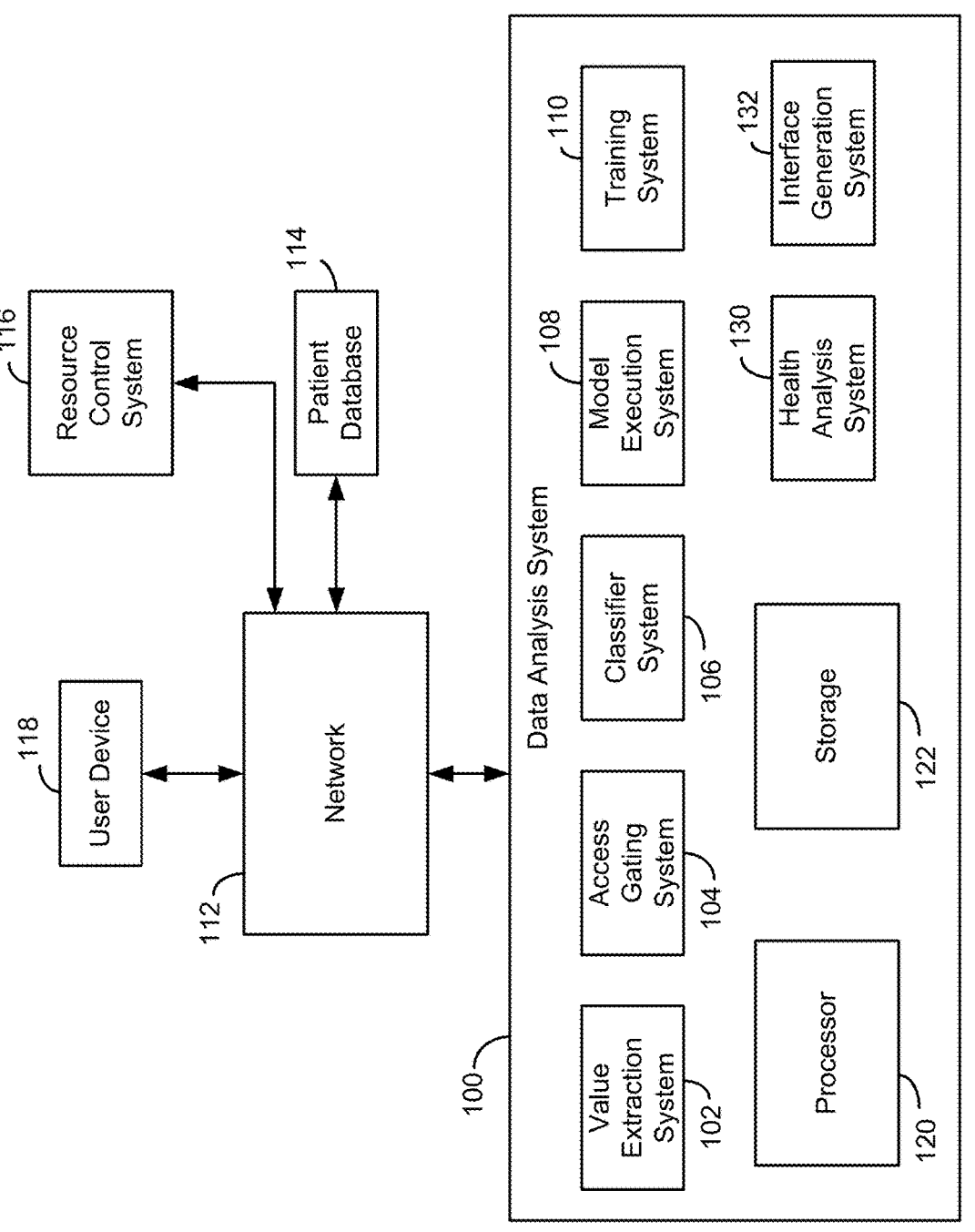
FIG. 1 illustrates a data analysis system facilitating a prediction of end of life, in accordance with certain aspects of the present inventive concept.

FIG. 1 illustrates a data analysis system 100 facilitating a prediction of end of life, in accordance with certain aspects of the present inventive concept. As shown, the data analysis system 100 may be in communication with a user device 118, resource control system 116, and patient database 114. A user device 118 (e.g., of a provider) may access the data analysis system through the network 112. As shown, the data analysis system 100 includes an access gating system 104. The resource control system 116 may communicate with the access gating system 104 to provide secure access of users (e.g., user device 118) to the data analysis system.

In the example shown, the data analysis system 100 may include storage 122 and processor 120. Storage 122 can include any storage device(s) for storing data. The storage 122 can store data from any of the components of the data analysis system 100. In some implementations, the processor 120 can include a central processing unit (CPU), a graphics processing unit (GPU), and/or a digital signal processor (DSP).

As shown, the data analysis system 100 may obtain patient data from a patient database 114 through the network. In some aspects, the data analysis system 100 may include a value extraction system 102 that obtains the patient data. The value extraction system 102 may extract patient data from the patient database 114 through the network. The classifier system 106 selects a subset of the patient data based on a characteristic of the patient. For instance, different patient data may be more relevant to end of life analysis for different types of patients (e.g., cancer patients or Alzheimer patients) and may be selected accordingly. Once the relevant data for the patient has been selected, the model execution system 108 uses a trained machine learning model to estimate end of life. In some cases, the data analysis system 100 may also include a training system 110 which may be used to train the machine learning model. For example, a training set may include patients' historical data and associated end of life data for the patients, which may be used to train the machine learning model, as described herein. The aspects of the present inventive concept may be implemented using any suitable machine learning model. For example, the machine learning model may be implemented using a decision tree or a neural network. The value extraction system 102, access gating system 104, classifier system 106, model execution system 108, and training system 110 may be implemented in hardware, software, or a combination of hardware and software.

In some aspects, the data analysis system 100 may include a health analysis system 130. The health analysis system 130 may analyze health records to identify patient health decline, similarities between health records, or discrepancies in health measurements, as described in more detail herein. The data analysis system 100 may also include an interface generation system 132. The interface generation system 132 may generate one or more user interfaces to indicate the results of health data analysis.

In some aspects, the value extraction system 102, access gating system 104, classifier system 106, model execution system 108, and training system 110 may be implemented by or in the same hardware, software, or combination of hardware and software (e.g., by a same processor). In some aspects, the value extraction system 102, access gating system 104, classifier system 106, model execution system 108, and training system 110 may be implemented by or in separate hardware, software, or combination of hardware and software.

Figure 2:
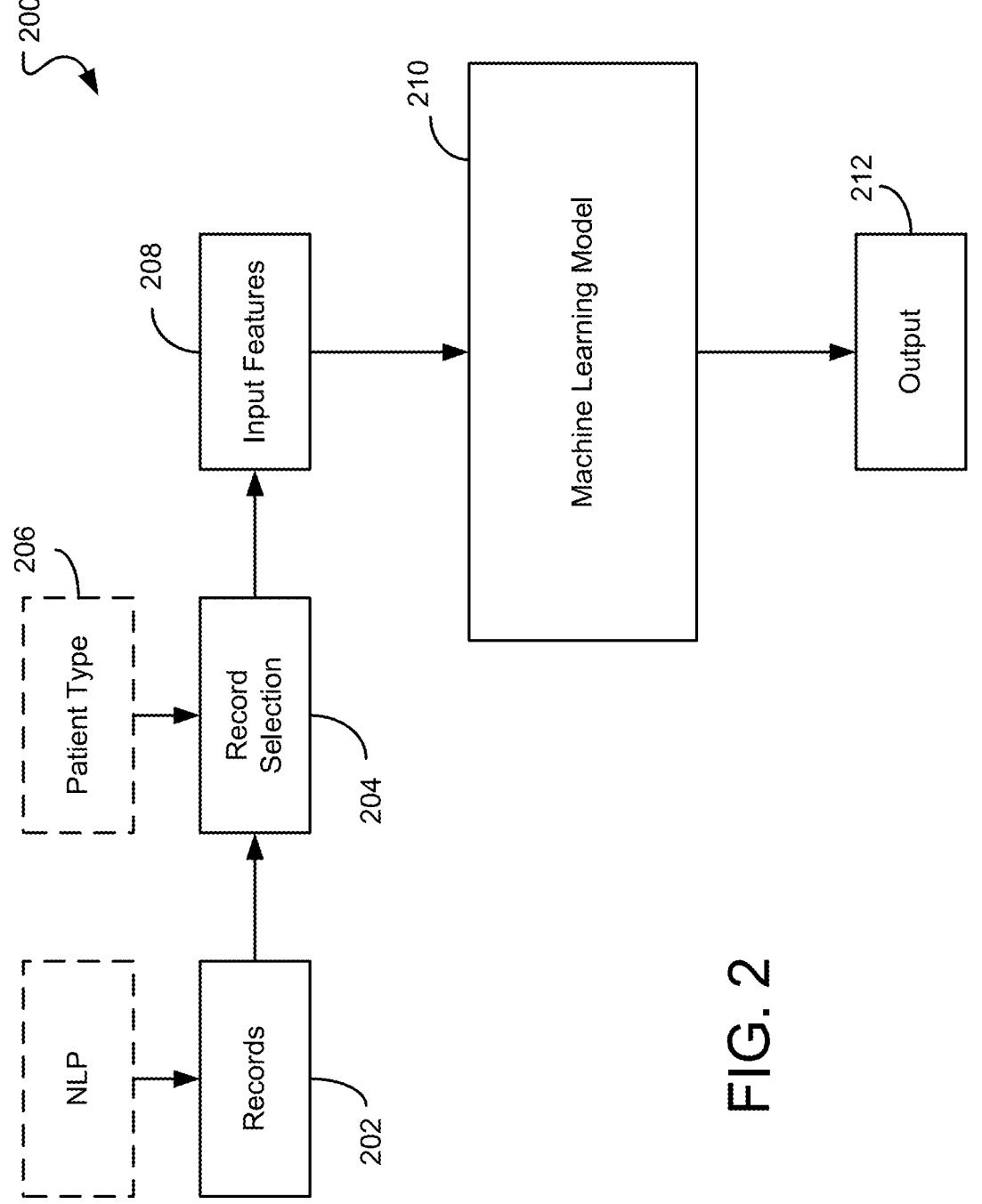
FIG. 2 illustrates example operations for end of life estimation, in accordance with certain aspects of the present inventive concept.

FIG. 2 illustrates example operations 200 for end of life estimation, in accordance with certain aspects of the present inventive concept. The operations 200 may be performed, for example, by the data analysis system 100. The data analysis system obtains records 202 and an indication of patient type 206 (e.g., cancer patient or Alzheimer patient). At block 204, the data analysis system selects a subset of the records 202 based on the patient type and generates input features 208 for the machine learning model 210. For instance, a subset of the records 202 may be more applicable for determining end of life for cancer patients as compared to Alzheimer patients, the subset of the records may be selected accordingly. The machine learning model executes using the input features 208 to generate an output 212 indicating end of life for the patient. In some cases, the output 212 may indicate a length of stay of the patient in a medical facility and may be used to determine financial data, as described herein.

In some cases, record 202 may be generated using natural language processing (NLP). For example, BLP may be used to extract information from notes (e.g., doctor or nurse notes). In some cases, the data analysis system may obtain records 202 from electronic medical records (EMR) of the patient. EMR captures information about patient health which may be used by the machine learning model to estimate end of life. Some features used for estimating end of life are primary diagnosis, co-morbidity (e.g., additional secondary diagnosis), age, gender, and functional assessments depending on the primary diagnosis. In some scenarios, if EMR captures palliative performance scale (PPS) or Braden Scale to indicate pressure ulcer risk and functional assessment staging tool (FAST) scores, these may be considered important features. Vitals captured at regular intervals may also play an important role in determining the status of patient health. Patient physical, emotional, functional, and spiritual state may be considered along with caregiver information that is obtained in the EMR. Thus, as described with respect to FIG. 1, a boosting classification algorithm may be used which is a high-performance boosting framework used in decision tree algorithms for ranking and classifying data. Since patients in hospice settings have similar basic features such as old age, severe life-threatening diseases that have progressed to an advanced stage and most have lost basic activities of daily living capabilities, the machine learning model for end of life prediction may be implemented using a leaf algorithm to reduce losses as compared to other gradient boosting algorithms. However, any suitable machine learning model may be used, such as a neural network.

In some cases, EMR may include categorical data such as age or PPS score with no numerical computation. Encoding may be applied to convert the categorical data into numerical values such as 0 and 1 which can be used to estimate end of line using machine learning. In some cases, if data for a particular patient is sparse (e.g., when the patient is first admitted), NLP may be applied on doctors notes, nurse notes, or any other comments in the EMR to extract key information about the patient condition, as described.

Figure 3:
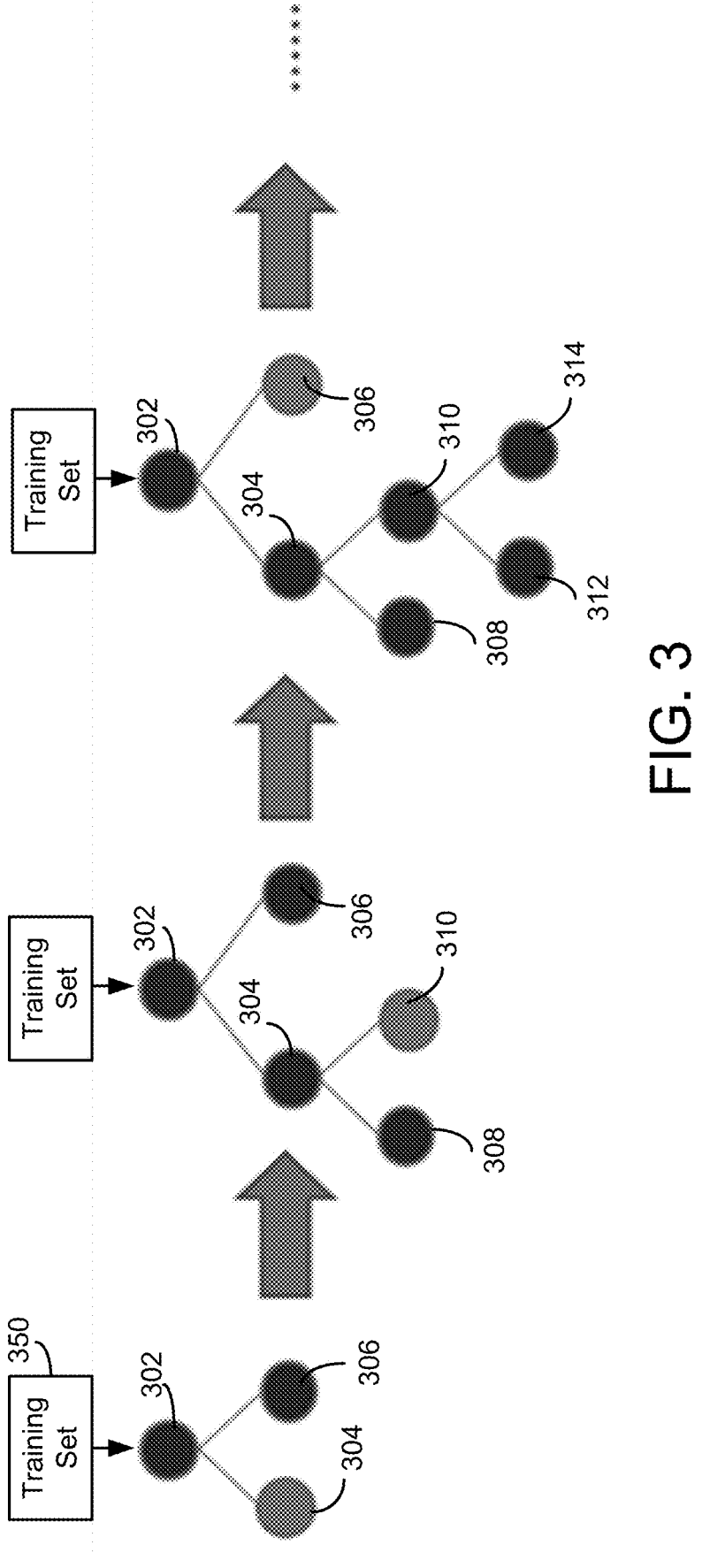
FIG. 3 illustrates example operations for training a decision tree using a leaf-wise tree growth technique, in accordance with certain aspects of the present inventive concept.

FIG. 3 illustrates example operations for training a decision tree using a leaf-wise tree growth technique, in accordance with certain aspects of the present inventive concept. A training set 350 may be provided to the decision tree. The training set may include patients' historical data and associated end of life data for the patients, which may be used to train the machine learning model as described herein. The decision tree includes various nodes such as nodes 302, 304, 306. At node 302, a particular criteria may be considered, such as whether the patient's age is over 80 years. If so, a particular output (e.g., end of life estimate) may be generated at node 306. As shown, node 304 may be further split using another criteria to generate nodes 308, 310, providing a leaf-wise decision tree growth. Node 310 may be further split into nodes 312, 314. In some cases, using leaf-wise tree growth, may result in the decision tree overfitting the training set. As a result, a max depth parameter may be used to determine when to split a particular node.

Figure 4:
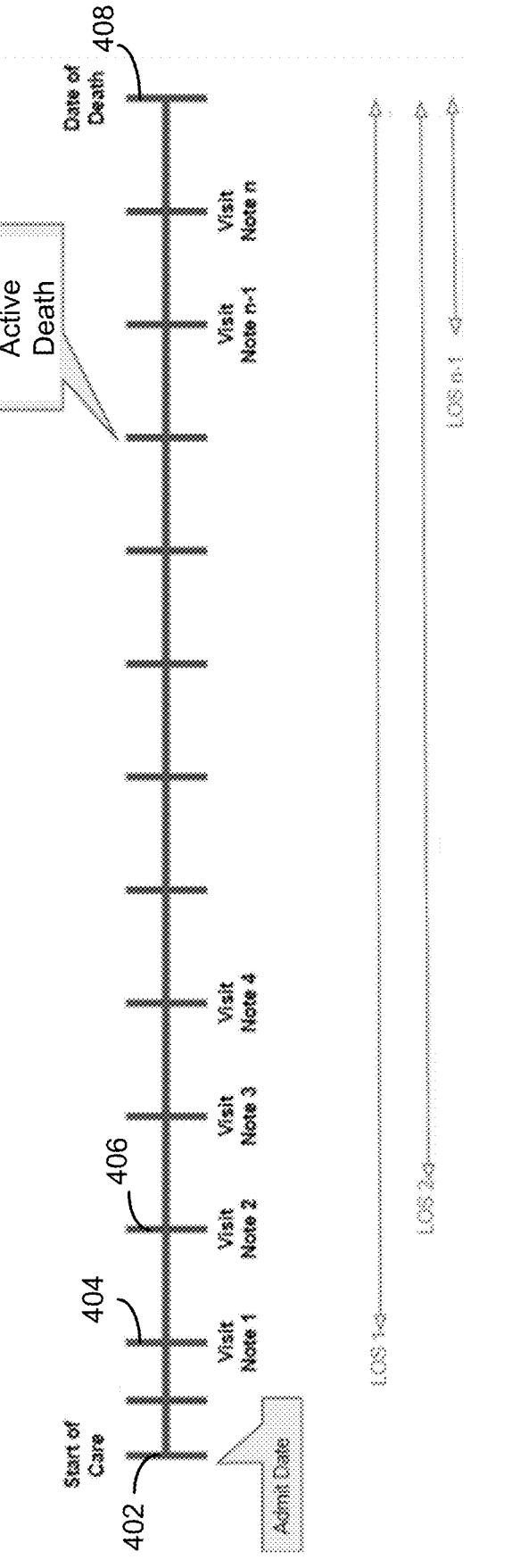
FIG. 4 illustrates a timeline associated with a patient stay, in accordance with certain aspects of the present inventive concept.

FIG. 4 illustrates a timeline associated with a patient stay, in accordance with certain aspects of the present inventive concept. As shown, start of care for a patient may begin at time 402. A patient may be admitted, and at various times throughout the patient's stay, nurse or doctor visits may occur during which patient notes are generated. At each visit, the patient's physical, emotional, functional, and spiritual state may be assessed. In some cases, after an initial length of stay (LOS) is estimated (e.g., upon start of care at time 402), one or more additional LOS estimations may occur as more information becomes available. For example, another LOS estimate may be generated after visit note 1 is generated at time 404, and another may be generated after visit note 2 is generated at time 406, and so on. Each LOS estimate may provide an estimate of the patient's date of death 408. The data analysis system analyzes the deterioration of the patient's condition with each visit and gives weight to important features. Example features that are important for estimating end of life for chronic obstructive pulmonary disease includes shortness of breath, cardio dyspnea, difficulty swallowing, irregular respiration, cough, respiratory orthopnea, diabetes, cardiac dysrhythmia, hypertension, gender, low oxygen, inability to cough, nebulizer, respiratory rate, irregular heart sound, exertion, or decreased strength. As shown, at one point in time, active death may occur. Active death refers to a period when patient vitals start to decline rapidly. The data analysis system described herein may estimate, upon admission of the patient, the date of death (e.g., end of life) which occurs after active death.

Figure 5:
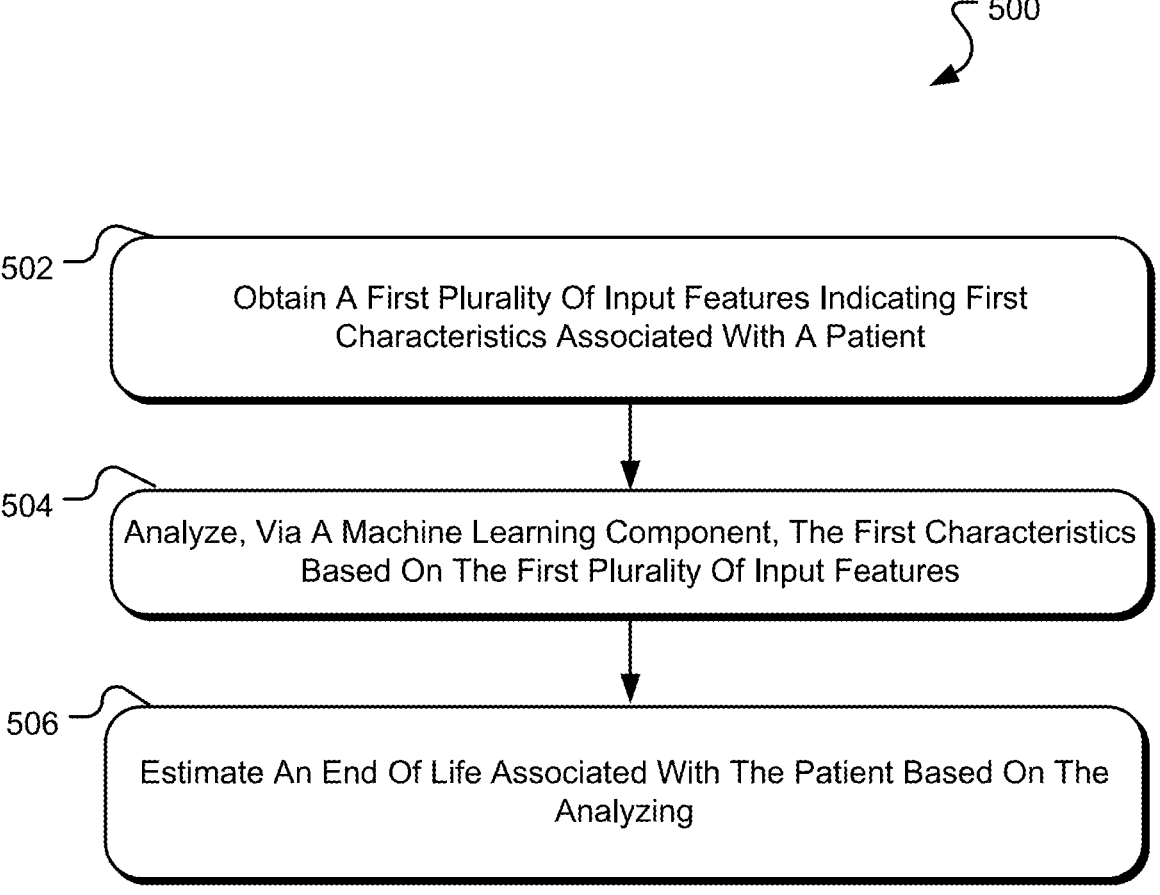
FIG. 5 is a flow diagram illustrating example operations for end of life prediction, in accordance with certain aspects of the present inventive concept.

FIG. 5 is a flow diagram illustrating example operations 500 for end of life prediction, in accordance with certain aspects of the present inventive concept. The operations 500 may be performed by, for example, a data analysis system such as data analysis system 100.

The operations 500 begin, at block 502, with the data analysis system obtaining a first plurality of input features (e.g., input features 208) indicating first characteristics associated with a patient. In the exemplary embodiment, the patient is a patient at a medical facility (e.g., a hospice patient). It is foreseen, however, that the patient may be a patient associated with another type of facility or a non-patient who is not associated with any facility (e.g., an individual) without deviating from the scope of the present inventive concept. As an example, the first plurality of input features may include at least one of a primary diagnosis, co-morbidity information, age, gender, and a functional assessment of the patient. In some cases, the data analysis system determines the first plurality of input features based on electronic medical records of the patient. In some aspects, the data analysis system selects (e.g., via the classifier system 106) a subset of information associated with the patient based on a type of the patient, and determines the first plurality of input features based on the subset of information. In some cases, the data analysis system generates the first plurality of input features by processing patient notes using natural language processing.

At block 504, the data analysis system analyzes, via a machine learning component, the first characteristics based on the first plurality of input features. In some cases, the machine learning component may be a decision tree machine learning component (e.g., as described with respect to FIG. 3). The decision tree machine learning component may be trained using a leaf-wise tree growth technique. At block 506, the data analysis system estimates an end of life associated with the patient based on the analysis at block 504.

In some aspects, the first plurality of input features indicates the first characteristics associated with the patient at a first point in time (e.g., time 402 at the admission of the patient as described with respect to FIG. 4). The data analysis system may obtain a second plurality of input features indicating second characteristics associated with the patient at a second point in time (e.g., time 404 when visit note 1 is generated) after the first point in time. The data analysis system may analyze, via the machine learning component, the second characteristics based on the second plurality of input features, and estimate a second end of life associated with the patient based on the analyzing. At least a portion of the first plurality of input features may be the same as at least a portion of the second plurality of input features.

Figure 6A:
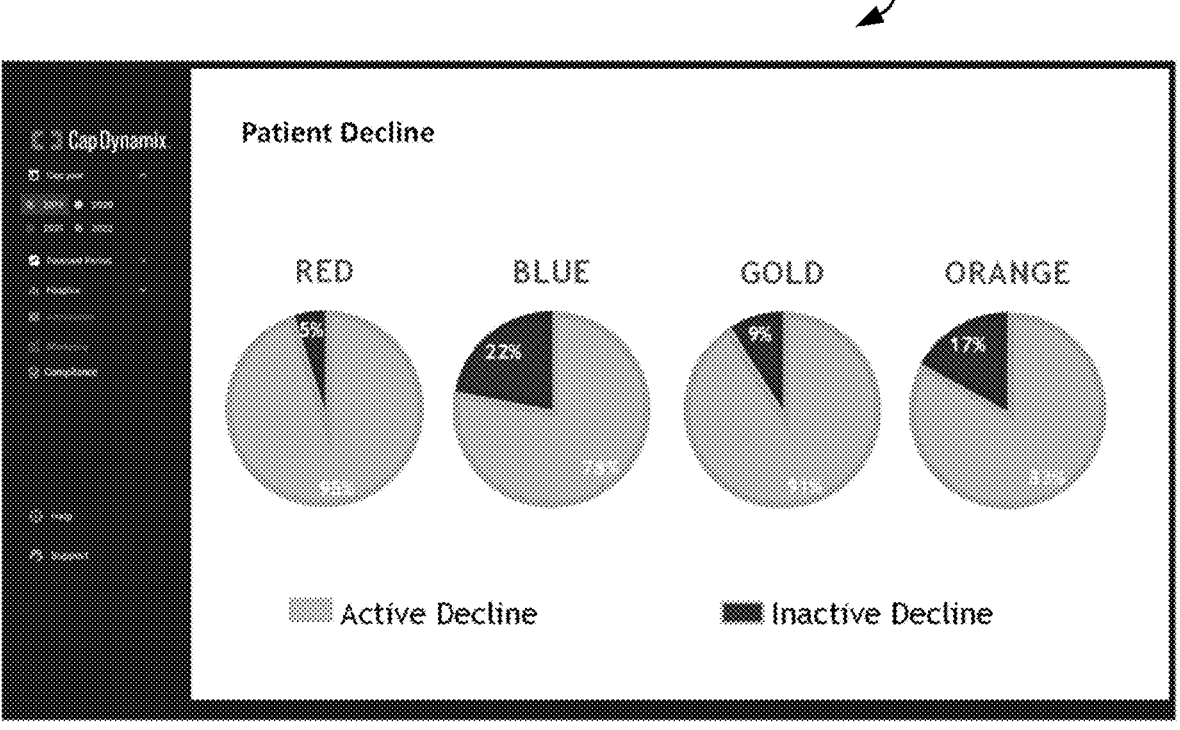
FIGS. 6A and 6B illustrate interfaces for indicating patient decline, in accordance with certain aspects of the present inventive concept.
Figure 6B:
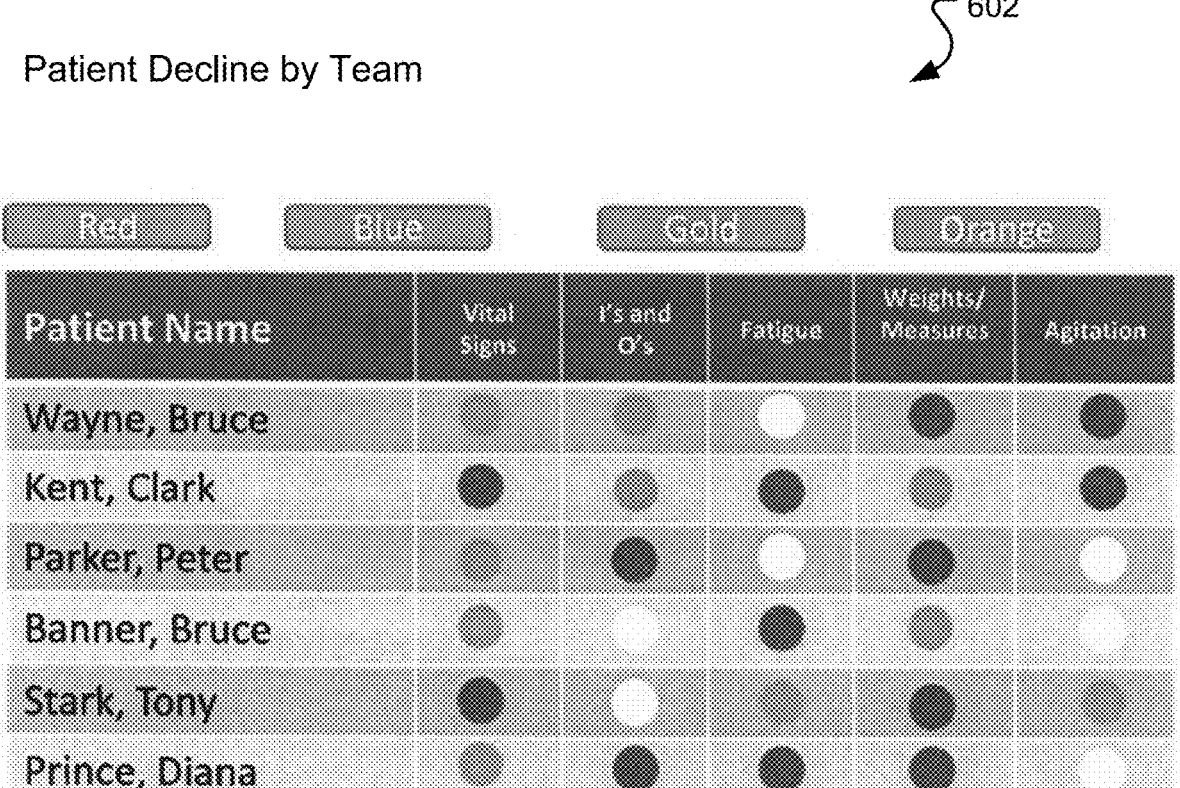

FIGS. 6A and 6B illustrate interfaces 600, 602, respectively, for indicating patient decline, in accordance with certain aspects of the present inventive concept. In some cases, hospices divide patients based on care groups. For instance, as shown in FIG. 6A, there may be a red team, blue team, gold team, and an orange team. In some aspects of the present inventive concept, the data analysis system 100 may identify, for each team, patient loads that are in the active process of dying (e.g., referred to as being in active decline). Hospice is designed for a certain length of stay (e.g., 90 days). Therefore, if a certain number of medical parameters are not showing health decline, then it may be determined that the patient is not in active decline, posing a risk that the hospice would have to prove whether the patient is worthy of staying in hospice care. Therefore, it is important to analyze medical parameters and provide clear indications of active decline to health practitioners. The interfaces 600, 602 flag patients that are not showing active decline with respect to one or more medical parameters in order for a compliance department to further analyze. For example, it may be shown that patient Clark is not declining with respect to three medical parameters and may be looked at more closely.

As shown in FIG. 6A, user interface 600 may indicate, for each team, what percentage of patients for that team are in active decline. A patient may be considered to be in active decline if a certain threshold number of medical parameters are showing health decline. Otherwise, the patient may be considered to be in inactive decline.

Figure 7:
FIG. 7 illustrates measurements of health parameters across time for a patient, in accordance with certain aspects of the present inventive concept.

In some aspects, information for various medical parameters may be received to identify patient decline. Any suitable medical parameters may be used, such as vital signs, inputs/outputs (e.g., how much a patient is eating and drinking/urinating and having bowel movements), fatigue, weights/measurements, and/or agitation. As shown in FIG. 6B, different thresholds of decline may be indicated for each medical parameter. For example, for each medical parameter, it may be indicated that the patient is in high decline, medium decline, or low decline. In some aspects, the health practitioner may be able to select a particular patient and receive additional details as shown in FIG. 7. FIG. 7 illustrates interface 700 indicating measurements of health parameters across time for a patient. A health practitioner may analyze the measurements to manage patient health.

Figure 8:
FIG. 8 illustrates a quality reporting interface, in accordance with certain aspects of the present inventive concept.

FIG. 8 illustrates a quality reporting interface 800, in accordance with certain aspects of the present inventive concept. As shown, the quality reporting interface 800 may provide various indications of quality issues. For instance, the quality reporting interface 800 may indicate whether medical records (e.g., nurse notes) show signs of copying and pasting of notes. Health practitioners merely copying and pasting notes (e.g., as opposed to entering new notes based on updated observations) poses a risk of failure to support a diagnosis in the future (e.g., when there is a request for additional documentation for supporting a claim). The data analysis system 100 may compare notes across time to identify similarities between the notes. The quality report interface 800 may notify management of specific health practitioners that are copying and pasting notes.

In certain aspects of the present inventive concept, the quality reporting interface 800 also indicates whether visit standards are being met and adhered to. For example, the data analysis system 100 may identify (receive) a plan of care and determine whether the plan of care is being adhered to. For instance, if the plan indicates that a patient is supposed to be visited a certain number of times a week, the data analysis system 100 may determine (e.g., based on a health practitioner chart) whether the patient is actually being visited per the plan and indicate whether the plan of care is being adhered to.

In some aspects, the quality reporting interface 800 may indicate a discrepancy in health records and provide notification of discrepancies accordingly. For example, if one health record (e.g., a measurement by a doctor) indicates a first blood pressure and another health record (e.g., a measurement by a nurse) indicates a second different health record (e.g., different by a certain threshold), a discrepancy in the documentation may be indicated and displayed so the discrepancy can be reconciled. In some instances, these types of discrepancies can be overcome by performing an imputation of data. The imputation can include back filling data gaps between the measurements (e.g., unpopulated data point times) with the last known measured data value.

Furthermore, one or more key features of the input features 208 can be determined, for instances, based on the patient type 206. For example . . . .

Figure 9:
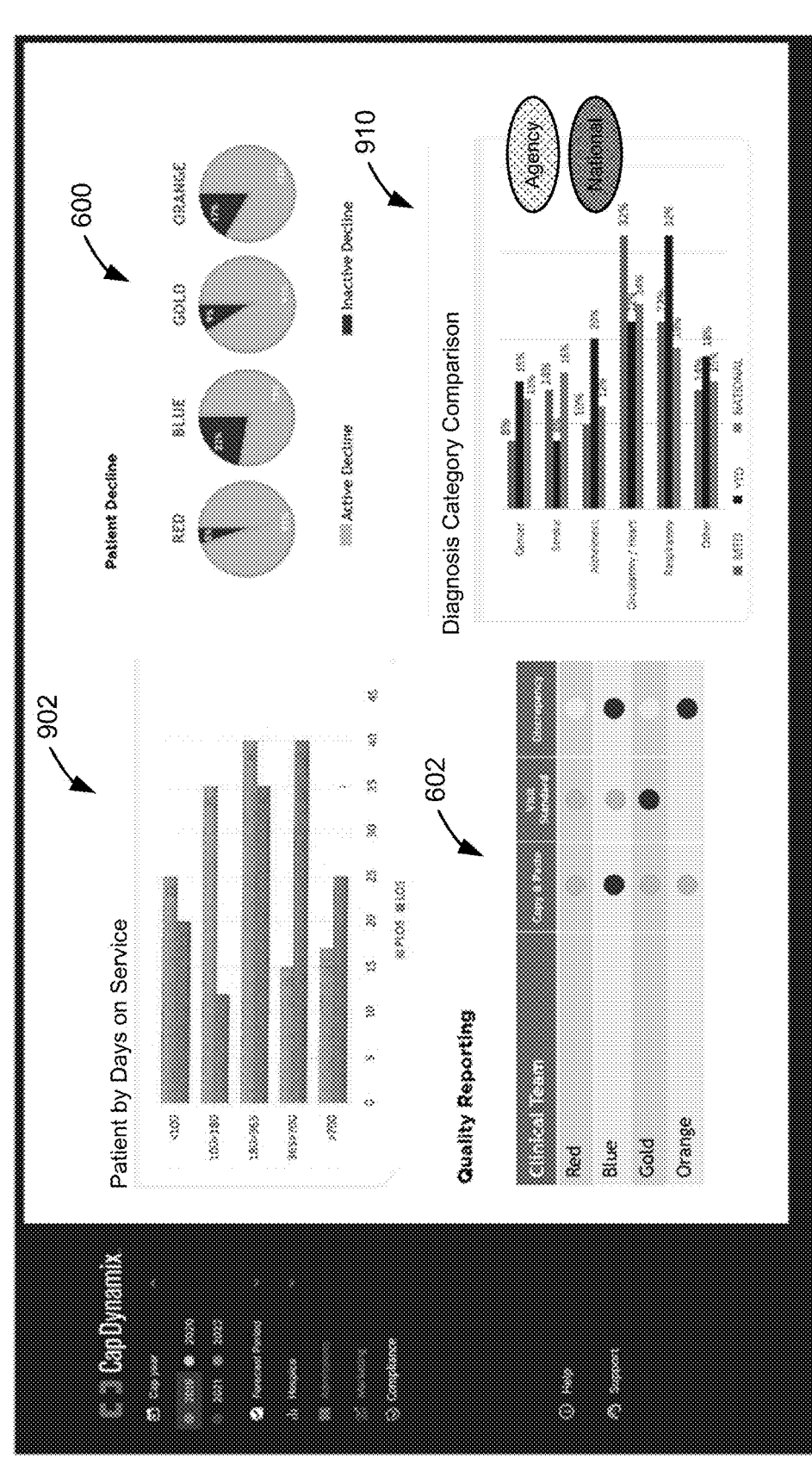
FIG. 9 illustrates a compliance dashboard, in accordance with certain aspects of the present inventive concept.

FIG. 9 illustrates a compliance dashboard 900, in accordance with certain aspects of the present inventive concept. As shown, the dashboard 900 may provide an interface 902 showing patients that have been on service for greater than 90 days and the percentage of the patients with specific health problems (e.g., cancer or stroke). The dashboard 900 may also show patient decline interfaces as described with respect to FIGS. 6A and 6B, as well as a matrix 910 of a mix of patients by diagnosis category as compared to national averages. For instance it may be indicated that 8% of patients are cancer patients month to date (MTD), 15% percent of patients are cancer patients year to date (YTD), and the national average of cancer patients in hospice care is 13%.

FIG. 10 is a flow diagram illustrating example operations 1000 for data analysis, in accordance with certain aspects of the present inventive concept. The operations 1000 may be performed by, for example, a data analysis system such as data analysis system 100.

The operations 1000 begin at block 1002, with the data analysis system obtaining health information associated with at least one patient of a health facility. At block 1004, the data analysis system analyzes the health information to determine a rate of health decline associated with one or more health parameters of the patient. At block 1006, the data analysis system generates at least one interface indicating whether the rate of health decline meets a threshold for each of the one or more health parameters. At block 1008, the data analysis system outputs the at least one interface for display on a display device.

In some aspects, the one or more health parameters include a plurality of health parameters. The data analysis system may determine whether the at least one patient is in active health decline based on whether a subset of the plurality of the health parameters indicate that the rate of health decline meets the threshold and yield a determination. The at least one interface may indicate whether the at least one patient is in active health decline based on the determination.

In some aspects, the patient may be one of multiple patients. The data analysis system may analyze health information to determine rates of health decline associated with the multiple patients. The at least one interface may indicate a percentage of the multiple patients that are in active health decline based on one or more of the rates of health decline meeting a threshold.

In some aspects, the data analysis system compares health records to identify similarities in descriptions to yield a comparison. The interface may indicate similar health records (e.g., copied and pasted records) based on the comparison. In some aspects, the data analysis system may compare patient care to a patient care plan. The interface may indicate whether the patient care plan is being adhered to based on the comparison. In some aspects, the data analysis system may identify discrepancies in health measurements in health records. The interface may indicate the discrepancies.

Figure 11:
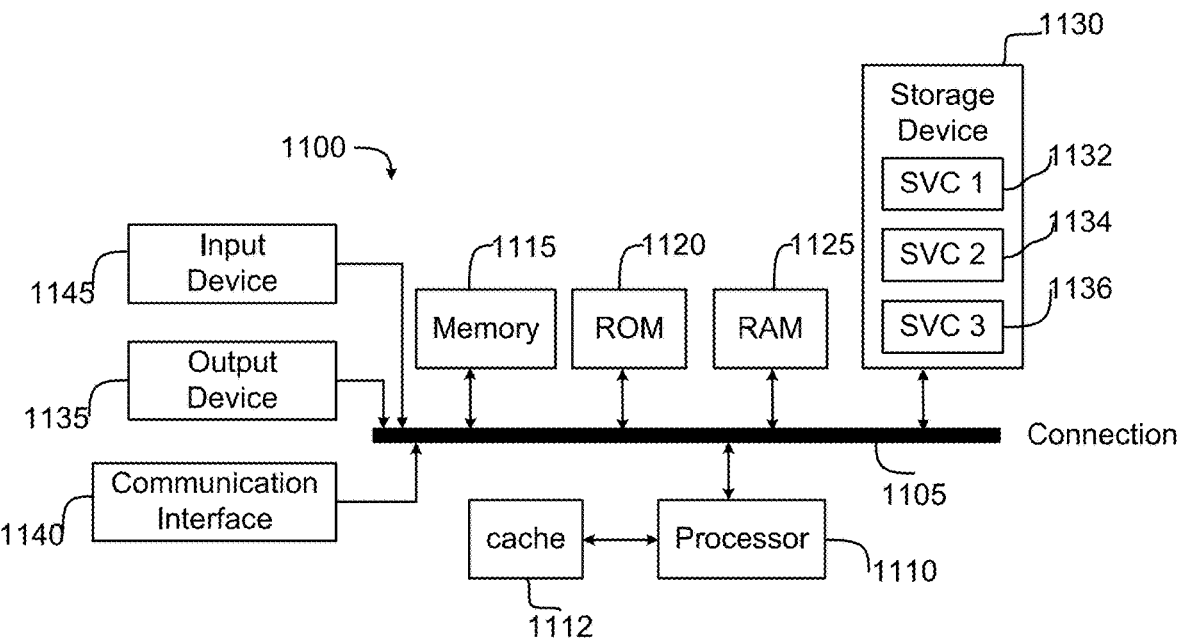
FIG. 11 illustrates an example architecture of a computing system.

FIG. 11 illustrates an architecture of a computing system 1100 wherein the components of the system 1100 are in electrical communication with each other using a connection 1105, such as a bus. Exemplary system 1100 includes a processing unit (CPU or processor) 1110 and a system connection 1105 that couples various system components including the system memory 1115, such as read only memory (ROM) 1120 and random access memory (RAM) 1125, to the processor 1110. The system 1100 can include a cache of high-speed memory connected directly with, in close proximity to, or integrated as part of the processor 1110. The system 1100 can copy data from the memory 1115 and/or the storage device 1130 to the cache 1112 for quick access by the processor 1110. In this way, the cache can provide a performance boost that avoids processor 1110 delays while waiting for data. These and other modules can control or be configured to control the processor 1110 to perform various actions. Other system memory 1115 may be available for use as well. The memory 1115 can include multiple different types of memory with different performance characteristics. The processor 1110 can include any general purpose processor and a hardware or software service, such as service 1 1132, service 2 1134, and service 3 1136 stored in storage device 1130, configured to control the processor 1110 as well as a special-purpose processor where software instructions are incorporated into the actual processor design. The processor 1110 may be a completely self-contained computing system, containing multiple cores or processors, a bus, memory controller, cache, etc. A multi-core processor may be symmetric or asymmetric.

To enable client interaction with the computing system 1100, an input device 1145 can represent any number of input mechanisms, such as a microphone for speech, a touch-sensitive screen for gesture or graphical input, keyboard, mouse, motion input, speech and so forth. An output device 1135 can also be one or more of a number of output mechanisms known to those of skill in the art. In some instances, multimodal systems can enable a client to provide multiple types of input to communicate with the computing system 1100. The communications interface 1140 can generally govern and manage the client input and system output. There is no restriction on operating on any particular hardware arrangement and therefore the basic features here may easily be substituted for improved hardware or firmware arrangements as they are developed.

Storage device 1130 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1125, read only memory (ROM) 1120, and hybrids thereof.

The storage device 1130 can include services 1132, 1134, 1136 for controlling the processor 1110. Other hardware or software modules are contemplated. The storage device 1130 can be connected to the system connection 1105. In one aspect, a hardware module that performs a particular function can include the software component stored in a computer-readable medium in connection with the necessary hardware components, such as the processor 1110, connection 1105, output device 1135, and so forth, to carry out the function.

Certain aspects described herein may be used for patients who are not eligible for hospice setting to improve their medical condition by predicting changes expected in the patient and providing intervention to prevent going to a state that will impact their health negatively. One example would be with a long term care facility or hospital setting.

These and various other arrangements will be described more fully herein. As will be appreciated by one of skill in the art upon reading the following disclosure, various aspects described herein can be a method, a computer system, or a computer program product. Accordingly, those aspects can take the form of an entirely hardware implementation, an entirely software implementation, or at least one implementation combining software and hardware aspects. Furthermore, such aspects can take the form of a computer program product stored by one or more computer-readable storage media (e.g., non-transitory computer-readable medium) having computer-readable program code, or instructions, included in or on the storage media. Any suitable computer-readable storage media can be utilized, including hard disks, CD-ROMs, optical storage devices, magnetic storage devices, and/or any combination thereof. In addition, various signals representing data or events as described herein can be transferred between a source and a destination in the form of electromagnetic waves traveling through signal-conducting media such as metal wires, optical fibers, and/or wireless transmission media (e.g., air and/or space).

Figure 12A:
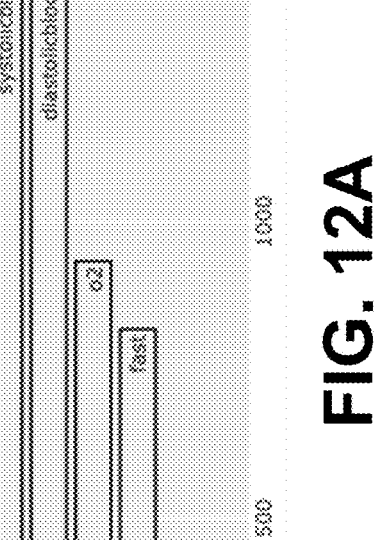
Figure 12B:
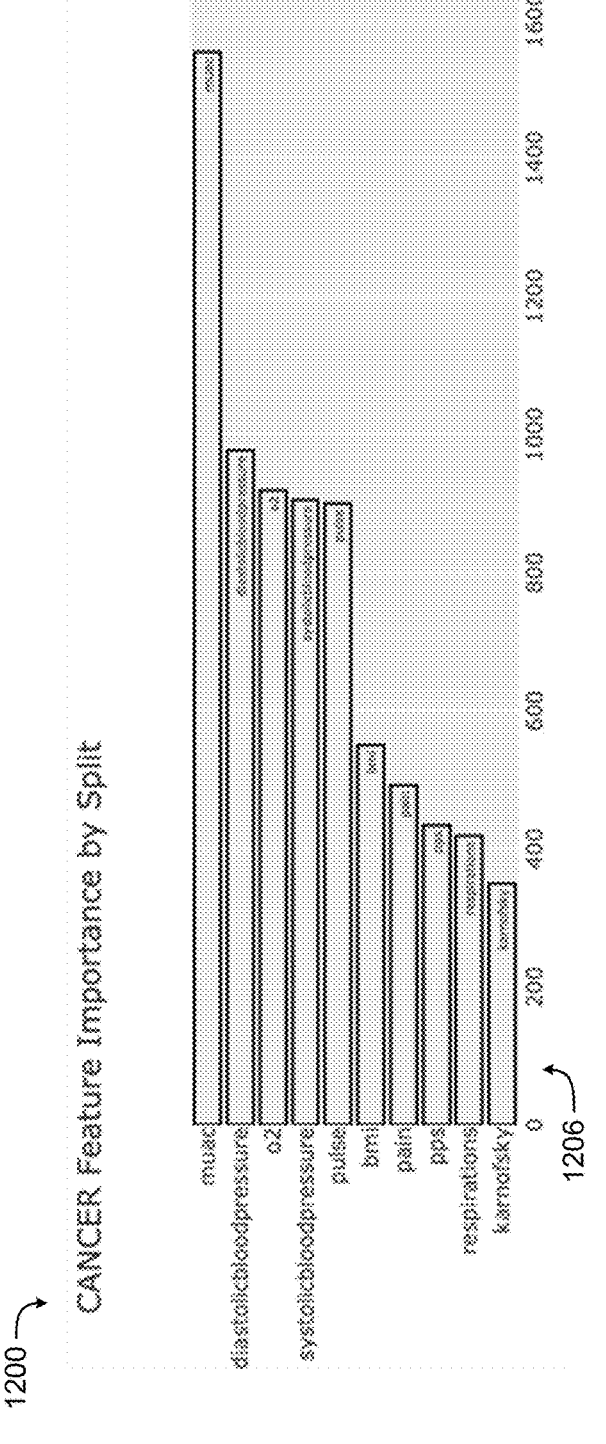

FIGS. 12A-12C illustrate example key features 1200 of the input features 208 which can correspond to particular patient types 206. The key features 1200 can be the output 212 resulting from the machine learning model 210 discussed above. Using the key features 1200 can reduce the multi-dimensionality of the data analysis system 100 by focusing/weighing the key features 1200 more than other input features 208 when assessing whether the input features 208 meet the decline threshold values.

For instance, FIG. 12A depicts example key features 1200 corresponding to an Alzheimer patient type. As depicted in FIG. 12A, the key features 1200 for the Alzheimer patient type can include a first key feature being a mid-upper arm circumference (MUAC) value; a second key feature being diastolic blood pressure value; a third key feature being a systolic blood value; a fourth key feature being fasting; a fifth key feature being an oxygen saturation level; a sixth key feature being a palliative performance scale (PPS); and/or a seventh key feature being a pain level. Furthermore, FIG. 12A depicts the importance of the key features 1200 by split in a first graph 1202 and the importance of the key features 1200 by gain in second graph 1204. The first graph 1202 can be generated by the machine learning model 210 wherein the default plot importance function uses split, the number of times a feature is used in a model. The second graph 1204 can be generated by the processor 120 wherein the gain-based feature importance is a standard metric, because it measures directly how much that feature contributes to the loss reduction.

Furthermore, FIG. 12B depicts example key features 1200 corresponding to cancer patient type. As depicted in FIG. 12B, the key features 1200 for the cancer patient type can include a first key feature being a mid-upper arm circumference (MUAC) value; a second key feature being a diastolic blood pressure value; a third key feature being an oxygen saturation value; a fourth key feature being a systolic blood pressure value; a fifth key feature being a pulse value; a sixth key feature being a body mass index value; a seventh key feature being a pain level value; an eight key feature being a PPS value; a ninth key feature being a respiration value; and/or a tenth key feature being a karnofsky performance status value. Furthermore, FIG. 12B depicts the importance of the key features 1200 by split in a first graph 1206 and the importance of the key features 1200 by gain in second graph 1208. The first graph 1206 can be generated by the machine learning model 210 wherein the default plot importance function uses split, the number of times a feature is used in a model. The second graph 1208 can be generated by the processor 120 wherein the gain-based feature importance is a standard metric, because it measures directly how much that feature contributes to the loss reduction.

Additionally, FIG. 12C depicts example key features 1200 corresponding to cancer patient type. As depicted in FIG. 12C, the key features 1200 for the cancer patient type can include a first key feature being a mid-upper arm circumference (MUAC) value; a second key feature being a systolic blood pressure value; a third key feature being pulse value; a fourth key feature being a diastolic blood pressure value; a fifth key feature being an oxygen saturation value; a sixth key feature being a body mass index value; a seventh key feature being a respiration value, an eight key feature being a PPS value; and/or a ninth key feature being a pain level value.

Implementations of the present inventive concept include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an implementation in the present inventive concept can be references to the same implementation or any implementation; and such references mean at least one of the implementations.

Reference to "one implementation" or "an implementation" means that a particular feature, structure, or characteristic described in connection with the implementation is included in at least one implementation of the disclosure. The appearances of the phrase "in one implementation" in various places in the specification are not necessarily all referring to the same implementation, nor are separate or alternative implementations mutually exclusive of other implementations. Moreover, various features are described which may be exhibited by some implementations and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various implementations given in this specification.

Without intent to limit the scope of the disclosure, examples of instruments, apparatus, methods and their related results according to the implementations of the present inventive concept are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

What is claimed is:

1. A method for end of life prediction comprising:

training a machine learning model, including a decision tree, using leaf-wise decision tree growth and a training data set of historical data for patients and associated end of life data of the patients, resulting in a trained machine learning model, at least one node of the decision tree of the trained machine learning model corresponding to an age threshold;

obtaining a first plurality of input features indicating first characteristics associated with a patient;

analyzing, via the trained machine learning model, the first characteristics based on the first plurality of input features; and estimating an end of life associated with the patient based on the analyzing via the trained machine learning model to generate an estimated end of life date;

estimating, based on the analyzing via the trained machine learning model, an active decline status or an inactive decline status; and using an interface generating system to present one or more graphical user interfaces including:

a first indication of the estimated end of life date, and a second indication of the active decline status or the inactive decline status.

2. The method of claim 1, further comprising:

determining the first plurality of input features based on electronic medical records of the patient.

3. The method of claim 1, further comprising:

selecting a subset of information associated with the patient based on a type of the patient; and determining the first plurality of input features based on the subset of information.

4. The method of claim 1, further comprising:

generating the first plurality of input features by processing patient notes using natural language processing.

5. The method of claim 1, wherein, the first plurality of input features indicates the first characteristics associated with the patient at a first point in time; and the method further comprises:

receiving a second plurality of input features indicating second characteristics associated with the patient at a second point in time after the first point in time;

analyzing, via the trained machine learning model, the second characteristics based on the second plurality of input features; and estimating a second end of life associated with the patient based on the analyzing.

6. The method of claim 1,
wherein,
the first plurality of input features includes baseline input features and additional input features used for continuous monitoring.

7. The method of claim 1,
wherein,
the first plurality of input features include at least one of a primary diagnosis, co-morbidity information, age, gender, and a functional assessment of the patient.

8. An apparatus for end of life prediction comprising:
a display:
a memory; and
one or more processors coupled to the memory, the one or more processors configured to:
train a machine learning model, including a decision tree, using leaf-wise decision tree growth and a training data set of historical data for patients and associated end of life data of the patients, resulting in a trained machine learning model, at least one node of the decision tree of the trained machine learning model corresponding to an age threshold;
obtain a plurality of input features indicating first characteristics associated with a plurality of patients;
analyze, via the trained machine learning model, the characteristics based on the first plurality of input features;
estimate an end of life date associated with a patient of the plurality of patients based on analyzing via the machine learning component;
estimate, based on the analyzing via the trained machine learning model, active decline statuses or an inactive decline statuses for the plurality of patients; and
present, via the display, one or more graphical user interfaces including:
a visual indication of the end of life date, and
a plurality of visual indicators, generated based on the plurality of input features, corresponding to a plurality of care teams, individual indicators of the plurality of visual indicators show a first percentage of patients of a particular care team having the inactive decline statuses or a second percentage of patients of the particular care team having the active decline statuses.

9. The apparatus of claim 8,
wherein,
the one or more processors are further configured to determine the plurality of input features based on electronic medical records of the patient.

10. The apparatus of claim 8,
wherein,
the one or more processors are further configured to:
select a subset of information associated with the patient based on a type of the patient, and
determine the plurality of input features based on the subset of information.

11. The apparatus of claim 8,
wherein,
the one or more processors are further configured to generate the plurality of input features by processing patient notes using natural language processing.

12. The apparatus of claim 8,
wherein, the plurality of input features are a plurality of input features,
the plurality of characteristics are a plurality of characteristics,
the plurality of input features indicates the first characteristics associated with the patient at a first point in time; and
the one or more processors are further configured to:
receive a second plurality of input features indicating second characteristics associated with the patient at a second point in time after the first point in time,
analyze, via the trained machine learning model, the second characteristics based on the second plurality of input features, and
estimate a second end of life associated with the patient based on the analyzing via the trained machine learning model.

13. The apparatus of claim 8,
wherein,
the patient is a hospice patient.

14. The apparatus of claim 8,
wherein,
the plurality of input features include at least one of a primary diagnosis, co-morbidity information, age, gender, and a functional assessment of the patient.

15. A non-transitory computer-readable medium having instructions stored thereon that, when executed by one or more processors, cause the one or more processors to:
train a machine learning model, including a decision tree, using leaf-wise decision tree growth and a training data set of historical data for patients and associated end of life data of the patients, resulting in a trained machine learning model, at least one node of the decision tree of the trained machine learning model corresponding to an age threshold;
obtain a plurality of input features indicating first characteristics associated with a patient;
analyze, via the trained machine learning model, the first characteristics based on the plurality of input features; and
estimate an end of life date associated with the patient based on the analyzing via the machine learning component;
perform a note comparison using the first plurality of input features; and
present, via a display, one or more graphical user interfaces including:
a visual indication of the end of life date, and
a quality reporting interface presenting an indication of whether medical records corresponding to the first plurality of input features show signs of copying and pasting based on the note comparison.

16. A data analysis system, comprising:
a memory; and
one or more processors coupled to the memory, the one or more processors being configured to:
train a machine learning model, including a decision tree, using leaf-wise decision tree growth and a training data set of historical data for patients and associated end of life data of the patients, resulting in a trained machine learning model, at least one node of the decision tree of the trained machine learning model corresponding to an age threshold;
obtain health information associated with at least one patient of a health facility;

analyze the health information, using the trained machine learning model, to determine a rate of health decline associated with one or more health parameters of the at least one patient;

analyze the health information, using the trained machine learning model, to determine whether the health information shows signs of copying and pasting; and present at least one graphical user interface including:

a first visual indicator indicating whether the rate of health decline meets a threshold for the one or more health parameters; and a second visual indicator indicating whether the health information shows signs of copying and pasting.

17. The data analysis system of claim 16, wherein, the one or more health parameters include a plurality of health parameters, the one or more processors are further configured to determine whether the at least one patient is in active health decline based on whether a subset of the plurality of the health parameters indicate that the rate of health decline meets the threshold and yield a determination, and the at least one interface indicates whether the at least one patient is in active health decline based on the determination.

18. The data analysis system of claim 16, wherein, the patient is one of multiple patients, the one or more processors are further configured to analyze health information to determine rates of health decline associated with the multiple patients, and the at least one interface indicates a percentage of the multiple patients that are in active health decline based on one or more of the rates of health decline meeting a threshold.

19. The data analysis system of claim 16, wherein, the one or more processors are further configured to compare health records to identify similarities in descriptions to yield a comparison, and the at least one interface indicates similar health records based on the comparison.

20. The data analysis system of claim 16, wherein, the one or more processors are further configured to compare patient care to a patient care plan to yield a comparison, and the at least one interface indicates whether the patient care plan is being adhered to based on the comparison.

21. The data analysis system of claim 16, wherein, the one or more processors are further configured to identify discrepancies in health measurements in health records, and the at least one interface indicates the discrepancies.

22. The method of claim 1, further comprising:

using, by the trained machine learning model, one or more key features weighed more than other features to reduce a dimensionality of the decision tree, the one or more key features corresponding to a patient type.

23. The method of claim 22, wherein:

the patient type an Alzheimer patient type or a cancer patient type, and the one or more key features include:

a mid-upper arm circumference value as a first key feature; and a blood pressure value as a second key feature.

* * * * *